United States Patent [19]

Mougin et al.

[11] Patent Number: 5,720,943
[45] Date of Patent: Feb. 24, 1998

[54] AQUEOUS DISPERSIONS OF RESINS, THEIR USE IN COSMETICS, AND COSMETIC COMPOSITIONS OBTAINED THEREFROM

[75] Inventors: Nathalie Mougin, Paris; Jean Mondet, Aulnay Sous Bois, both of France

[73] Assignee: L'Oreal, Paris, France

[21] Appl. No.: 418,296

[22] Filed: Apr. 7, 1995

[30] Foreign Application Priority Data

Apr. 7, 1994 [FR] France ................................. 94 04113

[51] Int. Cl.$^6$ .......................... A61K 7/04; A61K 7/025
[52] U.S. Cl. .......................... 424/61; 424/70.1; 424/70.7; 424/47; 424/59; 424/195.1; 424/401; 514/844; 514/845; 514/951
[58] Field of Search .................... 424/195.1, 61, 424/70.1, 70.7, 60, 63, 47, 59, 401; 514/844, 845, 951; 524/77; 530/201, 203; 106/124.62, 205, 218; 252/311, 312, 188.24

[56] References Cited

U.S. PATENT DOCUMENTS

| 1,230,599 | 6/1917 | Petroff ........................ 252/312 |
| 3,552,401 | 1/1971 | Michaelson et al. ............ 132/73 |
| 4,536,405 | 8/1985 | Nara et al. .................. 514/781 |
| 4,994,264 | 2/1991 | Verdon et al. ................ 424/63 |
| 4,996,004 | 2/1991 | Bucheler et al. ............. 252/314 |
| 5,053,218 | 10/1991 | Shernov ...................... 424/47 |
| 5,236,624 | 8/1993 | Lepert et al. ............... 252/314 |
| 5,439,672 | 8/1995 | Zabotto et al. ............... 424/59 |

FOREIGN PATENT DOCUMENTS 0 530 084  3/1993  European Pat. Off. .

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

Aqueous dispersions of resins of natural origin, their use in cosmetic compositions and cosmetic compositions obtained therefrom.

15 Claims, No Drawings

AQUEOUS DISPERSIONS OF RESINS, THEIR USE IN COSMETICS, AND COSMETIC COMPOSITIONS OBTAINED THEREFROM

The present invention relates to cosmetic compositions comprising, as a new ingredient, an aqueous dispersion of resin, also called pseudolatex. By "pseudolatex", there is understood to mean a dispersion consisting of generally spherical particles of polymer in an appropriate aqueous phase.

It is known to use synthetic polymer pseudolatexes in cosmetic compositions. These synthetic polymers are generally used for their advantageous properties as film-forming agents.

It is thus known, for example, to use aqueous emulsions of synthetic homo- and/or copolymers as a base for nail varnish (See JP 41/03511). Also known, for example, from EP 568035, is a composition containing an aqueous emulsion of synthetic polymers, in combination with a plasticizer, which can be used in cosmetic products such as nail varnishes or make-up.

The polymers used up until now were, however, all of synthetic origin. The inventors posed to themselves the problem of overcoming this disadvantage by avoiding the use of synthetic resins in cosmetic products, without adversely altering their qualities.

Natural resins of plant or animal origin constitute an advantageous class of product, by virtue of their special properties linked to their nature. It is however not apparent that these resins of natural origin can be used as they are in cosmetic compositions, given, in particular, the fact that they are generally insoluble in water, a solvent which is particularly used in the cosmetic industry.

The aim of the present invention is to solve this problem and to propose natural resins for use in the cosmetic field, these resins being provided in suitable form, namely in the form of aqueous dispersions.

The present invention is therefore drawn to an aqueous dispersion of resin of natural origin, alone or in the form of a mixture, selected from shellac resin, sandarac gum, elemis, dammars and copals.

The present invention is also drawn to processes for preparing these aqueous dispersions of natural resins, and further to their use in the cosmetic field in general, and in certain applications in particular.

The invention has the advantage of permitting the preparation of aqueous dispersions of stable natural resins, that is to say with no sign of flocculation, coalescence and/or sedimentation after several days of storage.

Furthermore, the use of a polymer in the form of a dispersion has the advantage of being able to work at a higher concentration, with a much more rapid drying time, this being due to the fact that it is possible to use less water while having a high concentration of film-forming polymer without encountering problems of viscosity, the polymer being in dispersion in the aqueous phase and not in solution.

In the remainder of the present description, the percentages are given by weight, unless otherwise stated.

As natural resin capable of being prepared as aqueous dispersion within the framework of the present invention, there may be mentioned shellac resin, sandarac resin, dammars, elemis or copals.

Shellac resin is an animal secretion, composed mainly of resin and wax, and is soluble in various organic solvents.

Sandarac gum is a resin which can be extracted from the bark of trees such as *Thuya articulata* or *Caliitris verrucosa*. It is composed mainly of acids such as pimaric acid, callitrolic acid and sandaricinic acid. It is insoluble in water but can be solubilized in organic solvents such as ethanol, acetone or ether.

Dammars are resins obtained from trees of the genera Damara or Shorea, and generally contain 62.5% resene (40% of solubles and 22.5% of insolubles in alcohol) and 23% acid.

Elemis are resins obtained from trees of the genus Icica and contain about 30% of various amyrins, 40% of resenes, as well as acids and essential oils.

Copals are resins extracted from various varieties of *Trachylobium verrucosum*, large trees of the family of leguminous plants similar to ash trees. Their main constituents are resinic acids. Resenes and essential oils are also present in their composition.

In general, the aqueous dispersions of natural resins are prepared in the following manner:

dissolution of the resin in an organic solvent whose boiling point is less than that of water, addition of water so as to form an oil-in-water emulsion, then selective evaporation of the organic solvent.

It is necessary to stabilize the emulsion obtained before the evaporation of the organic solvent. This can be done by adding surfactants, for example, when the natural resin does not contain ionizable groups, such as —COOH, —SO$_3$H or tertiary amine groups. The role of the surfactants is, in this case, also to stabilize the aqueous dispersion obtained. It is possible to use cationic or amphoteric surfactants, but preferably non-ionic surfactants such as a polyoxyethylene/polyoxypropylene copolymer, or anionic surfactants such as sodium lauryl sulphate.

The emulsion can also be stabilized by underneutralizing the resin, i.e., by neutralizing it only partially, which will cause self-stabilization of the emulsion. This is possible when the resin contains ionizable groups, as is the case for shellac resin. The under-neutralization can be performed by adding a non-volatile monobasic agent, such as an inorganic base such as sodium hydroxide or potassium hydroxide, or an amino alcohol chosen from the group consisting of 2-amino-2-methyl-1-propanol (AMP), triethanolamine, tri-isopropanolamine (TIPA), monoethanolamine, diethanolamine, tri-[(2-hydroxy)-1-propyl] amine, 2-amino-2-methyl-1,3-propanediol (AMPD) and 2-amino-2-hydroxymethyl-1,3-propanediol. It is thus possible to neutralize about 20 to 80% of the ionizable groups of the resin to stabilize the aqueous dispersion without solubilizing the polymer.

According to a first mode of preparing aqueous dispersions of natural origin according to the invention, an aqueous dispersion of shellac resin is prepared by dissolving resin in an organic solvent, adding water so as to form an emulsion, partially neutralizing the resin so as to self-stabilize the emulsion and then evaporating the organic solvent.

This preparation process is therefore carried out in the absence of surfactants as external stabilizers.

According to a second mode of preparing aqueous dispersions of natural origin according to the invention, an aqueous dispersion of sandarac gum is prepared by dissolving resin in an organic solvent, adding water containing a stabilizing surfactant so as to form a stable emulsion, and then homogenizing the emulsion so as to reduce the size of the particles, and evaporating the solvent.

It is thus possible to prepare aqueous dispersions of various natural resins, depending on whether these resins contain or otherwise ionizable groups. Depending on the nature of the resin and the subsequent use of the dispersion, it may be necessary to add to the said aqueous dispersion a plasticizing agent. This agent may be water-soluble or water-insoluble, and should be capable of solubilizing the resin. It is possible to add it either directly into the aqueous dispersion already formed, or during the stage for preparing as emulsion, before evaporating the solvent.

Among the plasticizing agents which can be used in the present invention, there may be mentioned:

the Carbitols from the company Union Carbide, namely Carbitol or diethylene glycol ethyl ether, methyl Carbitol or diethylene glycol methyl ether, butyl Carbitol or diethylene glycol butyl ether or alternatively hexyl Carbitol or diethylene glycol hexyl ether, the Cellosolves from the company Union Carbide, namely Cellosolve or ethylene glycol ethyl ether, butyl Cellosolve or ethylene glycol butyl ether, hexyl Cellosolve or ethylene glycol hexyl ether, the propylene glycol derivatives and in particular propylene glycol phenyl ether, propylene glycol diacetate, dipropylene glycol butyl ether, tripropylene glycol butyl ether as well as the Dowanols from the company Dow Chemical such as Dowanol PM or propylene glycol methyl ether, Dowanol DPM or dipropylene glycol ethyl ether, Dowanol TPM or tripropylene glycol methyl ether and Dowanol DM or diethylene glycol methyl ether, benzyl alcohol, triethyl citrate, 1,3-butylene glycol, diethyl, dibutyl and diisopropyl phthalates and adipates, diethyl and dibutyl tartrates, diethyl, dibutyl and 2-diethylhexyl phosphates, and glycerol esters such as glycerol diacetate (diacetin) and glycerol triacetate (triacetin).

Generally, 5 to 40% of plasticizing agent is introduced relative to the weight of resin dry matter.

The aqueous dispersions thus obtained can be used in any application, inter alia cosmetic applications, requiring the use of pseudolatex as partial or complete replacement of the synthetic resin pseudolatexes previously used.

It has indeed been discovered, surprisingly, that these aqueous dispersions of natural resins had good film-forming properties, comparable to those of the synthetic pseudolatexes normally used.

The formulation of the cosmetic compositions and the processes for preparing them will need to be optimized by persons skilled in the art on the basis of their general technical knowledge.

In particular, it is possible to use these aqueous dispersions in the preparation of hair products, such as hair-styling lotions or foams or lacquers, or alternatively in the preparation of makeup, such as mascara or nail varnish, or alternatively in treatment products such as face packs or treatment products for the nails.

It is possible to add to the cosmetic compositions comprising an aqueous dispersion according to the invention adjuvants, commonly used in the cosmetic industry, such as thickeners, UV-screening agents, perfumes, fillers, colorants and cosmetic pigments, in an amount of about 0.01–2%.

It is also possible to add actives, in an amount of 0.01–0.5%, among which there may be mentioned vitamins and derivatives thereof; biological materials and derivatives thereof such as keratin, proteins, hydrolysates, chitosan, melanin, hyaluronic acid, trace elements and collagen; glycerin; phospholipids.

The invention is illustrated in greater detail by, though not limited to, the following examples, which describe two processes for preparing aqueous dispersions of shellac resin and sandarac gum (Examples 1 and 2) and examples of the use of these aqueous dispersions in cosmetic compositions (Examples 3 to 7).

EXAMPLE 1

100 g of shellac resin (lac gum 55 Astra from KPS), having an acid value of 74, were dissolved in a mixture of 320 g of methyl ethyl ketone and 80 g of isopropanol, and then 9.37 g of 2-amino-2-methylpropanol were added so as to neutralize about 80% of the —COOH groups of the shellac resin.

The mixture thus obtained was stirred with the aid of a Moritz type disperser at 2500 revolutions per minute, and then an aqueous phase comprising 5 g of tripropylene glycol monomethyl ether in 390.6 ml of deionized water was introduced, over 15 minutes.

A self-stabilized emulsion was thus obtained which could be stirred for 15 minutes at a speed of 3000 revolutions per minute so as to complete the stabilization.

The organic solvents were then removed by evaporation at 50° C. under reduced pressure and 505 g of aqueous dispersion of shellac, of milky appearance, having the following characteristics, were obtained:

total dry extract level: 24% pH: 7.5 viscosity at 20° C. (Contraves): 1.5 mPa.s mean diameter of the particles: 90 nm size polydispersity of the particles: 0.20 (measured by quasi-elastic diffusion of light, with the aid of a COULTER N4 type apparatus)

EXAMPLE 2

1390 g of tetrahydrofuran and 48 g of tripropylene glycol monomethyl ether were mixed, and then 160 g of sandarac gum ("sandarac gum in tears" from EMIGA), having an acid value of 136, were added with stirring.

The solution obtained was filtered and was then stirred with the aid of a Moritz type disperser at 2500 revolutions per minute and an aqueous phase containing 66 g of sodium hydroxide, 3.2 g of sodium lauryl sulfate and 1320 ml of deionized water was introduced therein over 20 minutes.

The emulsion thus obtained was homogenized, so as to reduce the size of the fat globules, on a high pressure homogenizer at 700 bar, in two passes.

The organic solvents were then removed by evaporation at 40° C. under reduced pressure, and then the emulsion was concentrated until a dry extract of about 14% was obtained.

An aqueous dispersion of sandarac gum having the following characteristics was thus obtained:

total dry extract level: 14% mean particle diameter: 300 nm size polydispersity: 0.1 (measured by quasi-elastic diffusion of light with the aid of a COULTER N4 type apparatus).

EXAMPLE 3

An aerosol hair lacquer was prepared by packaging, in a suitable aerosol container:

| aqueous dispersion of shellac resin (Example 1) | 85.7 g |
| --- | --- |
| demineralized water | qs 100 g |

Pressure was applied by adding 30 g of dimethyl ether per 70 g of mixture.

A lacquer having the following characteristics was thus obtained: good removal on brushing, good removal on shampooing and good disentanglement.

EXAMPLE 4

A hair-styling lotion was prepared comprising

| aqueous dispersion of shellac resin (Example 1) | 75 g |
| --- | --- |
| perfume, colorant and preservative | qs |
| demineralized water | qs 100 g |

This lotion, which could optionally be provided in a pump dispenser, offered firm retention to the hair after application to wet hair or to dry hair.

EXAMPLE 5

An aerosol hair-styling foam having the following composition was prepared:

| aqueous dispersion of shellac resin (Example 1) | 25 g |
| --- | --- |
| perfume, colorant and preservative | qs |
| demineralized water | qs 100 g |

90 g of the composition obtained were introduced into an aerosol container without plunging tube. The valve was fixed and the container hermetically closed, and then 10 g of a butane/isobutane/propane propelling mixture (3.2 bar) were introduced.

The hair-styling foam obtained had good cosmetic characteristics.

EXAMPLE 6

A mascara having the following composition is prepared:

| part A | 11.5 g of triethanolamine stearate |
| --- | --- |
| | 7.0 g of beeswax |
| | 4.1 g of Carnauba wax |
| | 11.4 g of paraffin |
| part B | 5.5 g of black iron oxide |
| part C | 4.5 g of gum arabic |
| | 0.16 g of hydroxyethyl cellulose, Cellosize QP (Amerchol) |
| part D | 3.0 g of aqueous dispersion of shellac resin of Example 1 |
| preservatives | qs |
| water | qs 100.0 g |

The mascara was prepared by heating the ingredients of part A to 85° C., then adding part B and stirring with a turbine. The preparation water was then boiled, the preservatives added and then, at 85° C., the ingredients of part C. The aqueous phase obtained at 85° C. was then added to the mixture of parts A+B at 80° C., with stirring with the aid of a turbine (emulsification at 30° C.), then part D was added and mixed with the aid of a paddle.

A mascara cream was thus obtained which could be easily applied and which offered advantageous adhering qualities.

EXAMPLE 7

A mascara cream of the following composition was prepared in the same manner as above:

| part A | 11.5 g of triethanolamine stearate |
| --- | --- |
| | 7.0 g of beeswax |
| | 4.1 g of Carnauba wax |
| | 11.4 g of paraffin |
| part B | 5.0 g of black iron oxide |
| part C | 4.5 g of gum arabic |
| | 0.16 g of hydroxyethyl cellulose, Cellosize QP (Amerchol) |
| | 2.0 g of keratin hydrolysate, Kerasol (Coda) |
| part D | 2.0 g of aqueous dispersion of sandarac gum (Ex.2) |
| preservatives | qs |
| water | qs 100.0 g |

A mascara cream was thus obtained which could be easily applied and which had advantageous adhering qualities.

EXAMPLE 8

A treatment product for the nails having the following composition was prepared, simply by mixing and stirring:

| aqueous dispersion of shellac resin (Example 1) | 91.2 g |
| --- | --- |
| glycerin | 3 g |
| calcium protein | 0.3 g |
| wheat hydrolysate | 0.2 g |
| chitosan derivative | 0.3 g |
| water | 5 g |

This composition could be easily applied to the nail and made it possible to obtain, after drying, a dry and brilliant film which could be easily removed with water.

Daily application of this composition to the nail made it possible, after several weeks, to improve the general condition of the nails.

What is claimed is:

1. A stable aqueous dispersion of spherical particles of resin of natural origin, said spherical particles comprising one or more resins, said one or more resins being shellac resin, sandarac gum, elemi, or copals.

2. An aqueous dispersion according to claim 1, wherein said resin contains ionizable groups and wherein said ionizable groups are partially neutralized.

3. A process for preparing a stable aqueous dispersion of spherical particles of shellac resin, comprising the steps of:
   (a) dissolving said resin in an organic solvent;
   (b) adding water to the solution formed in step (a) in order to form an emulsion;
   (c) partially neutralizing the ionizable groups of said resin, said partial neutralization occurring before or during addition of water to said resin, said addition of water forming a self-stabilized emulsion with said resin; and
   (d) evaporating the organic solvent.

4. A process for preparing a stable aqueous dispersion of spherical particles of sandarac gum, comprising the steps of:
   (a) dissolving the gum in an organic solvent to form a solution;
   (b) adding water to said solution to form an emulsion of particles of said gum and a surfactant to stabilize said emulsion;
   (c) homogenizing said emulsion to reduce the size of said particles; and (d) evaporating the solvent.

5. A cosmetic composition comprising a stable aqueous dispersion of spherical particles of resin of natural origin, said spherical particles comprising one or more resins, said one or more resins being shellac resin, sandarac gum, elemi, or copals.

6. The cosmetic composition of claim 5, wherein the composition is a hair product composition.

7. The cosmetic composition of claim 6, wherein the composition is an aerosol lacquer, a hair-styling lotion, or a hair-styling foam.

8. The cosmetic composition of claim 5, wherein the composition is a make-up composition.

9. The cosmetic composition of claim 8, wherein the composition is a mascara or a nail varnish.

10. The cosmetic composition of claim 5, wherein the composition is a product for the treatment of the hair, nails, or skin.

11. The cosmetic composition of claim 10, wherein the composition is a face mask or a nail treatment base.

12. A stable aqueous dispersion of spherical particles of resin of natural origin, said spherical particles comprising one or more resins, said one or more resins being shellac resin, sandarac gum, elemi, dammars or copals, wherein said dispersion of improved stability is obtained by a process comprising the steps of:

(a) dissolving said resin in an organic solvent;

(b) adding water to the solution obtained in step (a) to form an emulsion, optionally adding a surfactant to stabilize said emulsion;

(c) optionally partially neutralizing the resin before or during the addition of water in step (b); and (d) evaporating said organic solvent.

13. A stable aqueous dispersion of spherical particles according to claim 12, wherein said resin contains ionizable groups and wherein said ionizable groups are partially neutralized.

14. A cosmetic composition comprising a stable aqueous dispersion of spherical particles of resin of natural origin, said dispersion comprising one or more resins said one or more resins being shellac resin, sandarac gum, elemi, dammars or copals, wherein said stable dispersion is obtained by a process comprising the following steps:

(a) dissolving said resin in an organic solvent;

(b) adding water to the solution obtained in step (a) to form an emulsion; optionally adding a surfactant to stabilize said emulsion;

(c) optionally partially neutralizing the resin before or during the addition of water in step (b); and (d) evaporating said organic solvent.

15. A process for preparing a stable aqueous dispersion of particles of resin of natural origin, comprising one or more resins, said one or more resins being shellac resin, sandarac gum, elemi, dammars or copals, wherein said dispersion of improved stability is obtained by a process comprising the steps of:

(a) dissolving said resin in an organic solvent;

(b) adding water to the solution obtained in step (a) to form an emulsion, optionally adding a surfactant to stabilize said emulsion;

(c) optionally neutralizing the resin before or during the addition of water in step (b); and (d) evaporating said organic solvent.

* * * * *